(12) United States Patent
Hu

(10) Patent No.: US 9,737,215 B2
(45) Date of Patent: Aug. 22, 2017

(54) REFLECTIVE SENSING MODULE HAVING LIGHT CHIP AND SENSOR CHIP MOUNTED TO BOTTOM SURFACE OF TRANSPARENT TOP COVER, AND WRISTBAND COMPRISING SAID REFLECTIVE SENSING MODULE

(71) Applicant: Dyi-Chung Hu, Hsinchu (TW)

(72) Inventor: Dyi-Chung Hu, Hsinchu (TW)

( * ) Notice: Subject to any disclaimer, the term of this patent is extended or adjusted under 35 U.S.C. 154(b) by 0 days.

(21) Appl. No.: 15/074,327

(22) Filed: Mar. 18, 2016

(65) Prior Publication Data

US 2016/0296117 A1 Oct. 13, 2016

Related U.S. Application Data

(60) Provisional application No. 62/145,257, filed on Apr. 9, 2015.

(51) Int. Cl.
*A61B 5/00* (2006.01)

(52) U.S. Cl.
CPC .......... *A61B 5/0059* (2013.01); *A61B 5/6824* (2013.01); *A61B 5/6831* (2013.01); *A61B 2562/0238* (2013.01); *A61B 2562/12* (2013.01); *A61B 2562/164* (2013.01)

(58) Field of Classification Search
CPC ................ A61B 5/0059; A61B 5/6824; A61B 2562/0238; H01L 21/67259; H01L 27/14678; G01J 1/44; G01J 3/02
USPC ... 250/221, 227.14, 227.24, 214.1, 551, 239
See application file for complete search history.

(56) References Cited

U.S. PATENT DOCUMENTS

| | | | | |
|---|---|---|---|---|
| 4,340,813 A | * | 7/1982 | Sauer ..................... | B60K 37/00 250/221 |
| 5,661,303 A | * | 8/1997 | Teder ..................... | G01N 21/43 250/227.25 |
| 2014/0231635 A1 | | 8/2014 | Kerness et al. | |

* cited by examiner

*Primary Examiner* — Que T Le
(74) *Attorney, Agent, or Firm* — Jianq Chyun IP Office

(57) ABSTRACT

A reflective sensing module is disclosed which can be embedded in a wristband for sensing a health information of a person wearing it. The health information can be wireless transmitted directly or indirectly to the internet for a further process. The reflective sensing module comprises a top glass, a bottom circuitry configured on a bottom surface of the top glass, a light chip and a sensor chip are electrically coupled with the bottom circuitry of the top glass; wherein the light chip emits light beams upwards passing through the top glass to an object; the sensor chip detects reflective light beams downwards passing through the top glass for a further process.

20 Claims, 12 Drawing Sheets

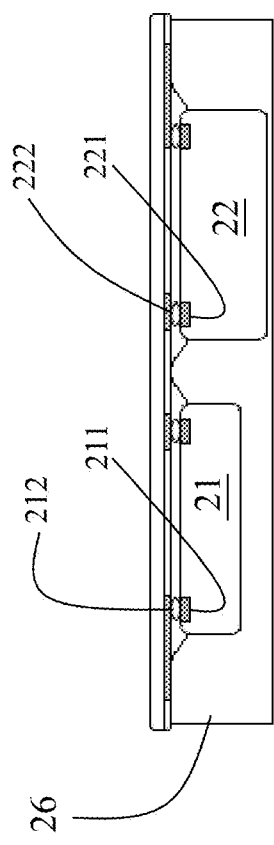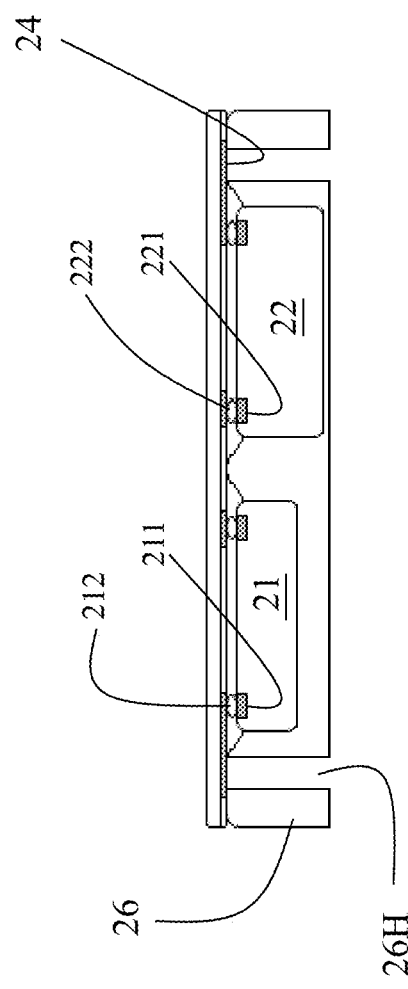
Fig.2C
Fig.2D

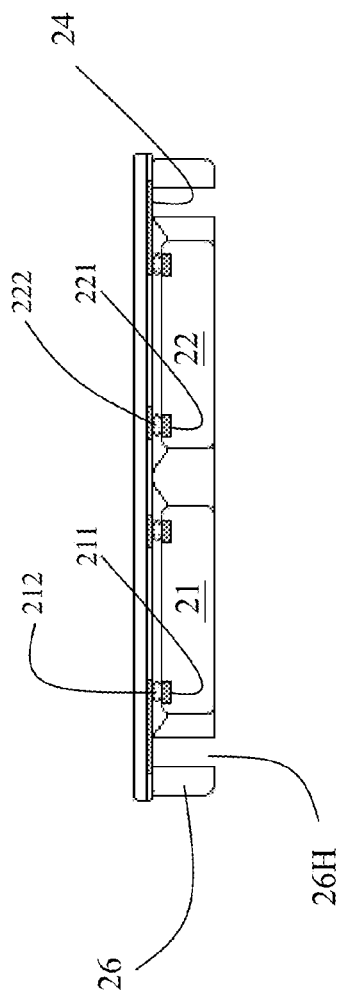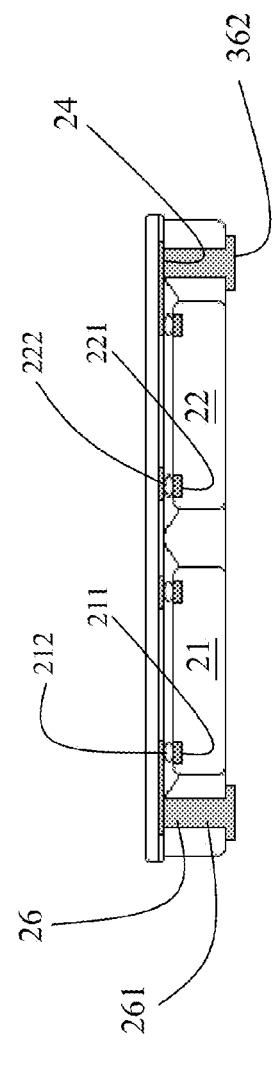

REFLECTIVE SENSING MODULE HAVING LIGHT CHIP AND SENSOR CHIP MOUNTED TO BOTTOM SURFACE OF TRANSPARENT TOP COVER, AND WRISTBAND COMPRISING SAID REFLECTIVE SENSING MODULE

RELATED APPLICATIONS

The present application claims the benefit of U.S. Provisional Application No. 62/145,257, filed Apr. 9, 2015, the disclosure of which is hereby incorporated by reference herein in its entirety.

BACKGROUND

Technical Field

The present invention relates to a sensing module, especially relates to a reflective sensing module having a light chip and a sensor chip mounted on a top glass substrate.

Description of Related Art

FIG. 1 show a prior art

FIG. 1 shows a prior art US 20140231635 publication which discloses an optical device 110-1 configured in a first cavity 108-1 and a sensor die 110-3 configured in a second cavity 108-3 of a carrier substrate 104.

FIG. 1 illustrates a silicon carrier substrate 104 having cavities 108-1, 108-3. An optical device 110-1 disposed within the cavity 108-1 and a sensor die 128 disposed within the cavities 108-3. A cover 112 is disposed on top of the carrier substrate 104. Lens 114-1. 114-2 may be configured on top of the dies 110-1, 110-3. Through-substrate-vias (TSV) 116-1, 116-2 extends through the carrier substrate 104 to corresponding contact pads 118 on the bottom surface of cavity 108-1. Solder bumps 120 electrically connect the optical device 110-1 and pad 118. Through-substrate-vias (TSV) 116-3, 116-4 extends through the carrier substrate 104 to the redistribution circuit 122 on the bottom surface of cavity 108-3. The sensor die 110-3 stacks on a top of a processor die 128. Through-substrate-vias (TSV) 126 extends through the processor die 128 for an electrical connection among the sensor die 110-3, processor die 128 and redistribution circuit 122. The disadvantages of the prior art is that two cavities needs to be made in the carrier substrate 104. The cavities' forming process is complicated. A simpler device or process is desired to be developed in the sensing module industry.

BRIEF DESCRIPTION OF THE DRAWINGS

FIG. 2A-2G shows a fabrication process for a first embodiment according to the present invention.

FIG. 3A-3G shows a fabrication process for a second embodiment according to the present invention.

DETAILED DESCRIPTION OF THE INVENTION

FIG. 2A-2G shows a fabrication process for a first embodiment according to the present invention.

Figure 1:
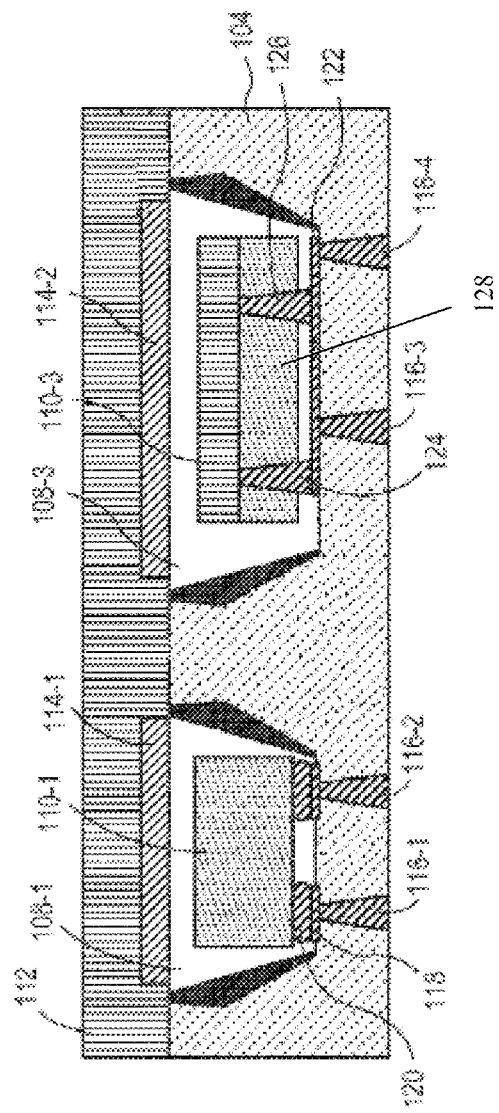
FIG. 1 show a prior art.
Figure 2A:
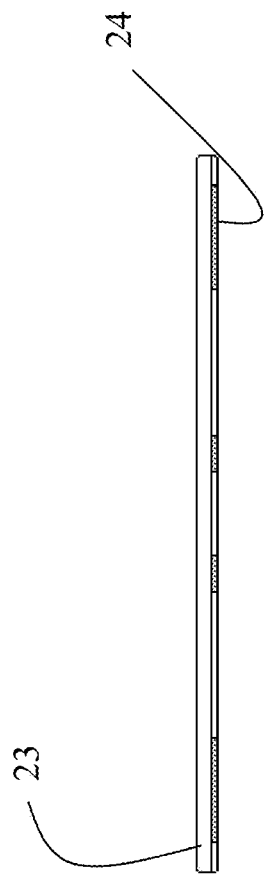

FIG. 2A shows a transparent top cover such as a glass 23 is prepared. A bottom circuitry 24 is configured on a bottom surface of the top glass 23.

Figure 2B:
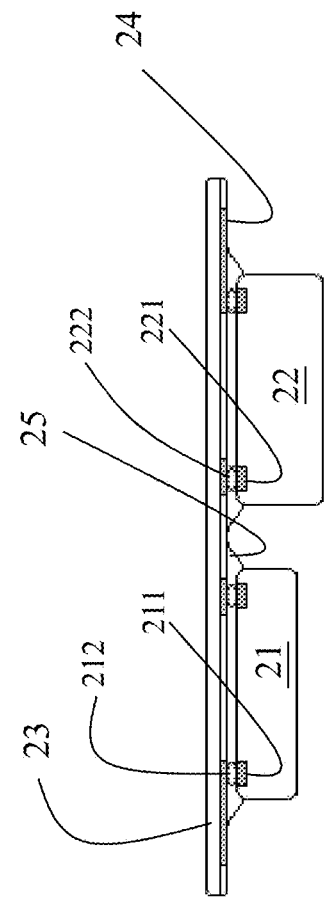

FIG. 2B shows a light chip 21 electrically coupled to the bottom circuitry 24; wherein the light chip 21 has a plurality of top electrodes 211 electrically coupled to the bottom circuitry 24 of the top glass 23 through solder ball 212; and a sensor chip electrically coupled to the bottom circuitry 24; wherein the sensor chip 22 has a plurality of top electrodes 221 electrically coupled to the bottom circuitry 24 of the top glass 23 through solder ball 222.

The light chip 21 used in the present invention can be one of light emitting diode, laser diode, vertical cavity surface emitting laser (VCSEL) or the like. Different underfill material can be chosen for a specific light chip 21. For example, an infrared (IR) light transparent underfill material such as silicone or benzocyclobutene (BCB) can be used to fill in the gap between the light chip 21 and the top glass 23 for a module where an IR light chip is used.

FIG. 2C shows a molding compound 26 is applied to enclose the light chip 21 and the sensor chip 22.

FIG. 2D shows a plurality of holes 26H are made through the molding compound 26 to expose predetermined areas of the bottom circuitry 24.

Figure 2E:
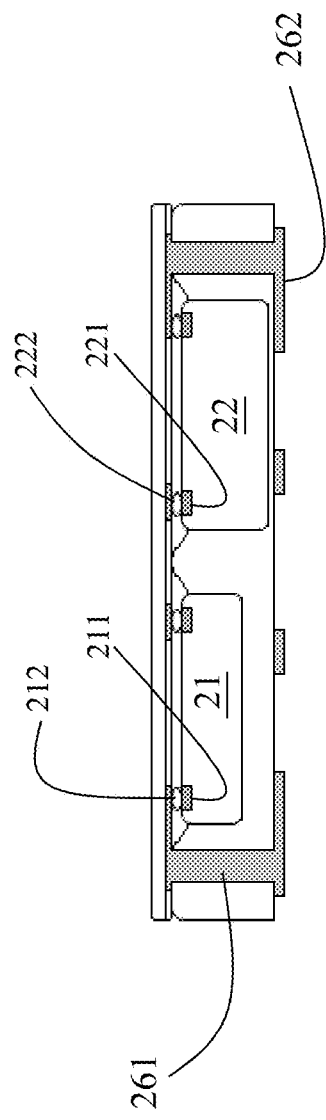

FIG. 2E shows metal plated or filled in each hole 26H so that a plurality of via metals 261 are formed passing through the molding compound 26. A top of the via metal 261 electrically couples to the bottom circuitry 24 of the top glass 23. A bottom circuitry 262 is formed on a bottom surface of the molding compound 26. The bottom circuitry 262 is electrically coupled to a bottom of the via metal 261.

Figure 2F:
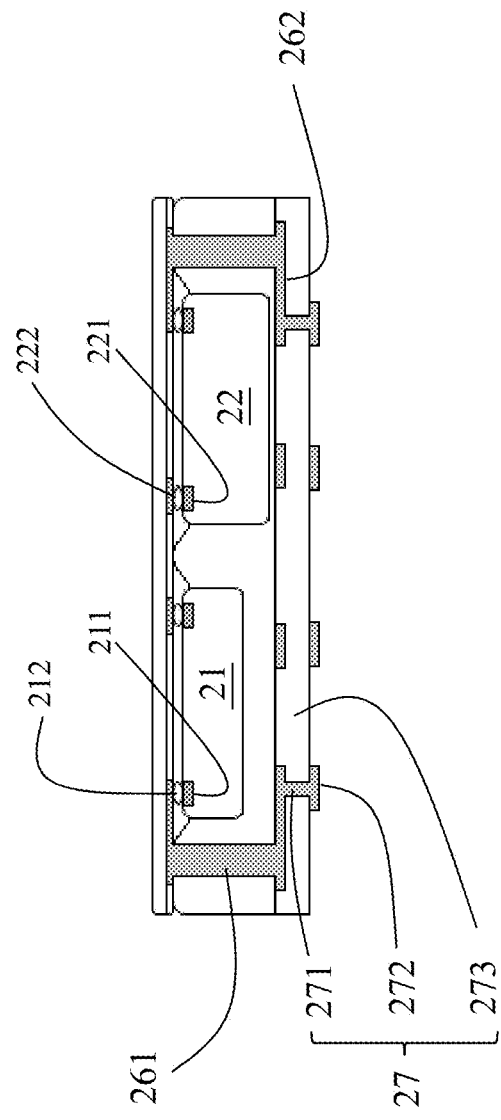

FIG. 2F shows a redistribution layer 27 formed on bottom of the bottom circuitry 262 of the molding compound 26. The redistribution layer 27 includes redistribution circuitry 271, dielectric layer 273 and a plurality of bottom pads 272. The redistribution circuit 271 is embedded in the dielectric layer 273, and a plurality of bottom pads 272 are formed on a bottom of the dielectric layer 273. Each bottom pad 272 is electrically coupled to the redistribution circuity 271.

Figure 2G:
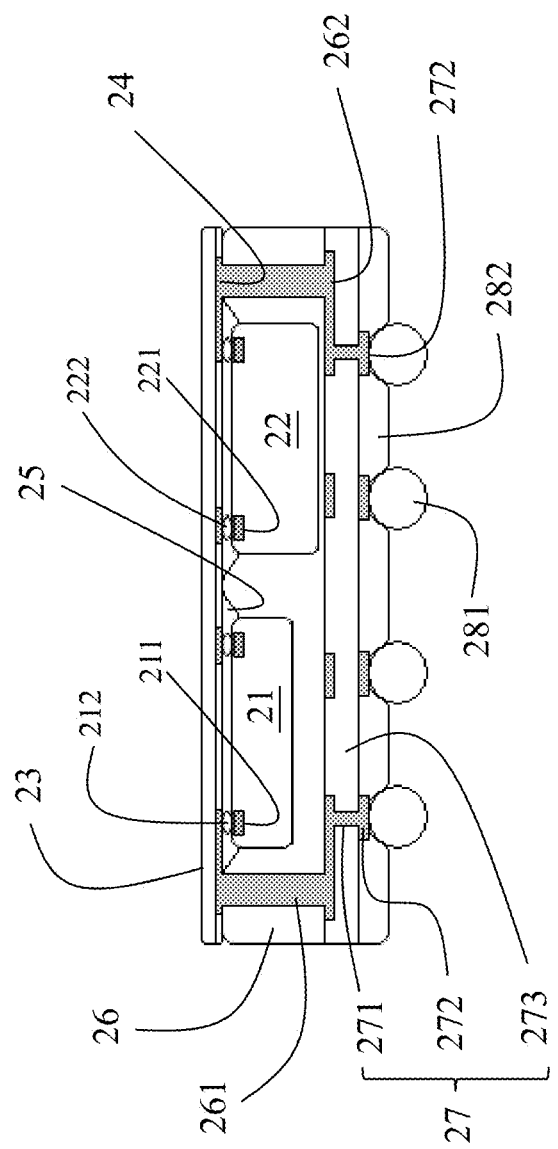

FIG. 2G shows a plurality of solder balls 281, each solder ball 281 is configured on one corresponding bottom pad 272. The light chip 21 is able to emit a plurality of light beams upwards passing through the top glass 23 to an object (not shown) on top. The sensor chip 22 detects reflective light beams downwards passing through the top glass 23 for a further processing.

FIG. 3A-3G shows a fabrication process for a second embodiment according to the present invention.

Figure 3A:
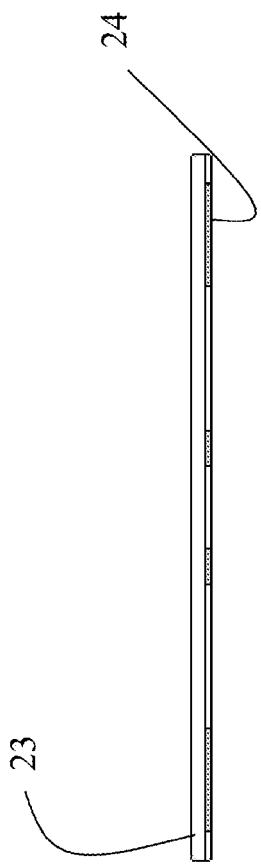

FIG. 3A shows a top glass 23 is prepared; and a bottom circuitry 24 is configured on a bottom surface of the top glass 23.

Figure 3B:
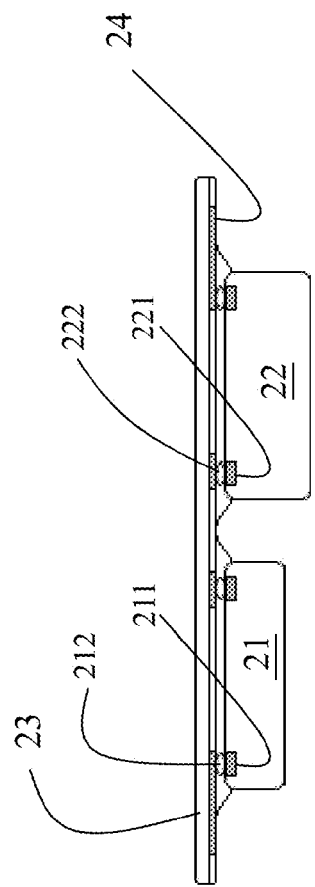

FIG. 3B shows a light chip 21 electrically coupled to the bottom circuitry 24; wherein the light chip 21 has a plurality of top electrodes 211 electrically coupled to the bottom circuitry 24 of the top glass 23 through solder ball 212; and a sensor chip electrically coupled to the bottom circuitry 24; wherein the sensor chip 22 has a plurality of top electrodes 221 electrically coupled to the bottom circuitry 24 of the top glass 23 through solder ball 222.

Figure 3C:
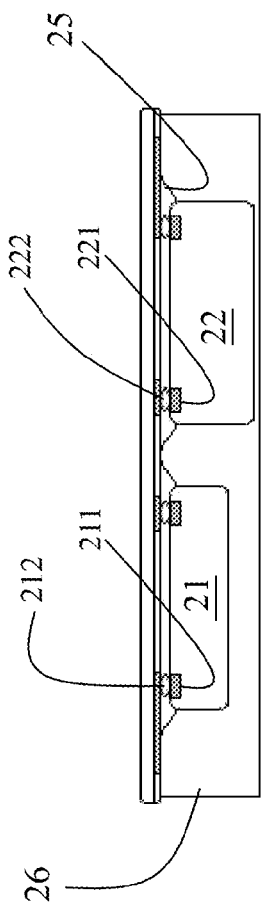

FIG. 3C shows a molding compound 26 is applied to enclose the light chip 21 and the sensor chip 22.

Figure 3D:
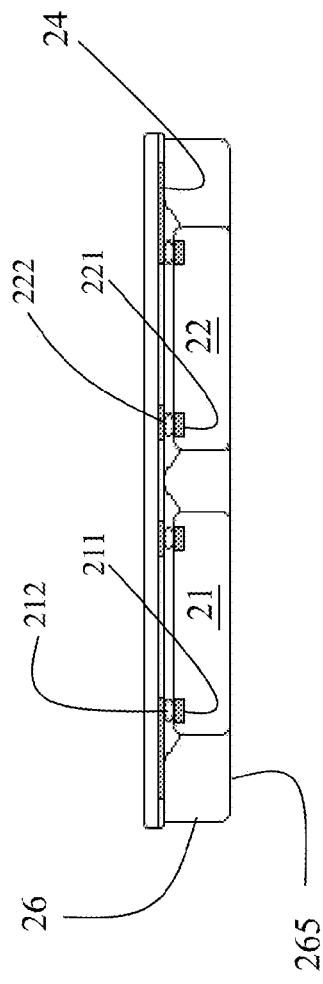

FIG. 3D shows a thinning process is applied from bottom to expose a bottom surface of the light chip 21 and the sensor chip 22. A flat bottom 265 is formed where the bottom surface of the molding compound 26, the bottom surface of the light chip 21, and the bottom surface of the sensor chip 22 are made coplanar.

FIG. 3E shows a plurality of holes 26H are made through the molding compound 26 to expose predetermined areas of the bottom circuitry 24.

FIG. 3F shows metal filled or plated in each hole 26H so that a plurality of via metals 261 are formed passing through the molding compound 26. A top end of the via metal 261 is electrically couple to the bottom circuitry 24 of the top glass 23. A bottom circuitry or bottom pad 362 is formed on a bottom surface of the molding compound 26. The bottom pad 362 is electrically coupled to a bottom end of the via metals 261.

Figure 3G:
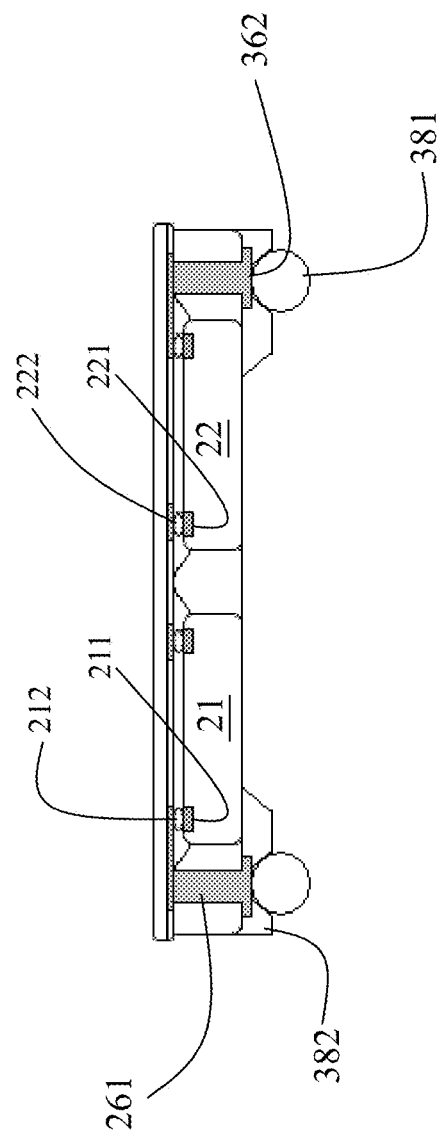

FIG. 3G shows a plurality of solder balls 381, each solder ball 381 is configured on one corresponding bottom pad 362. The light chip 21 is able to emit a plurality of light beams upwards passing through the top glass 23 to an object (not shown) on top. The sensor chip 22 detects reflective light beams downwards passing through the top glass 23 for a further processing.

Figure 4:
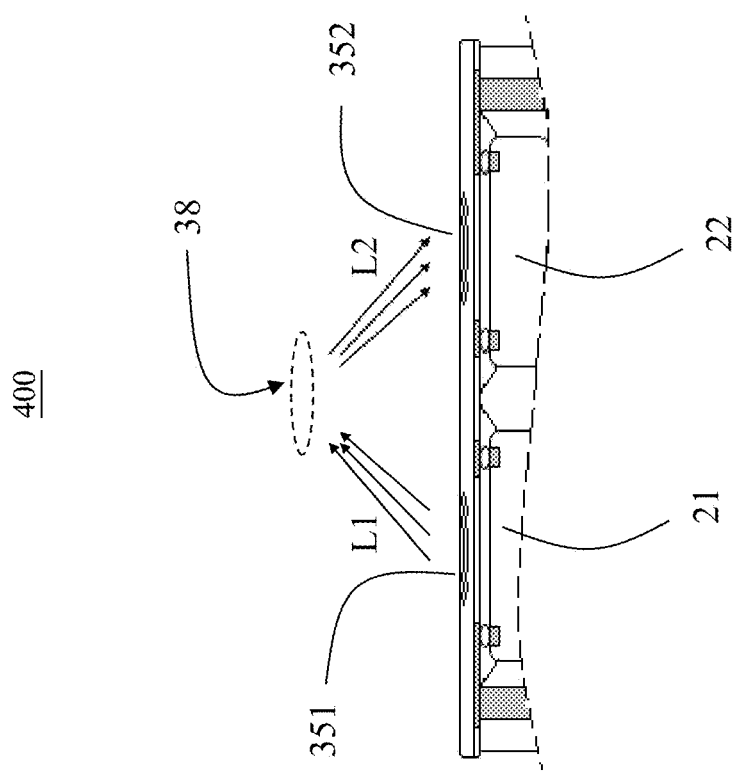
FIG. 4 shows a modified version of the embodiments according to the present invention.

FIG. 4 shows a modified version of the embodiments according to the present invention.

FIG. 4 shows a modified version 400 of the reflective sensing module. A first Fresnel lens 351 is configured on top of the light chip 21; and a second Fresnel lens 352 is configured on top of the sensor chip 22. The first Fresnel lens 351 focuses the plurality of light beams L1 from the light chip 21 into a detecting area 38 where an object (not shown) to be detected is configured. A plurality of reflective light beams L2 reflected from the object (not shown) is detected by the sensor chip 22 for a further process.

Figure 5:
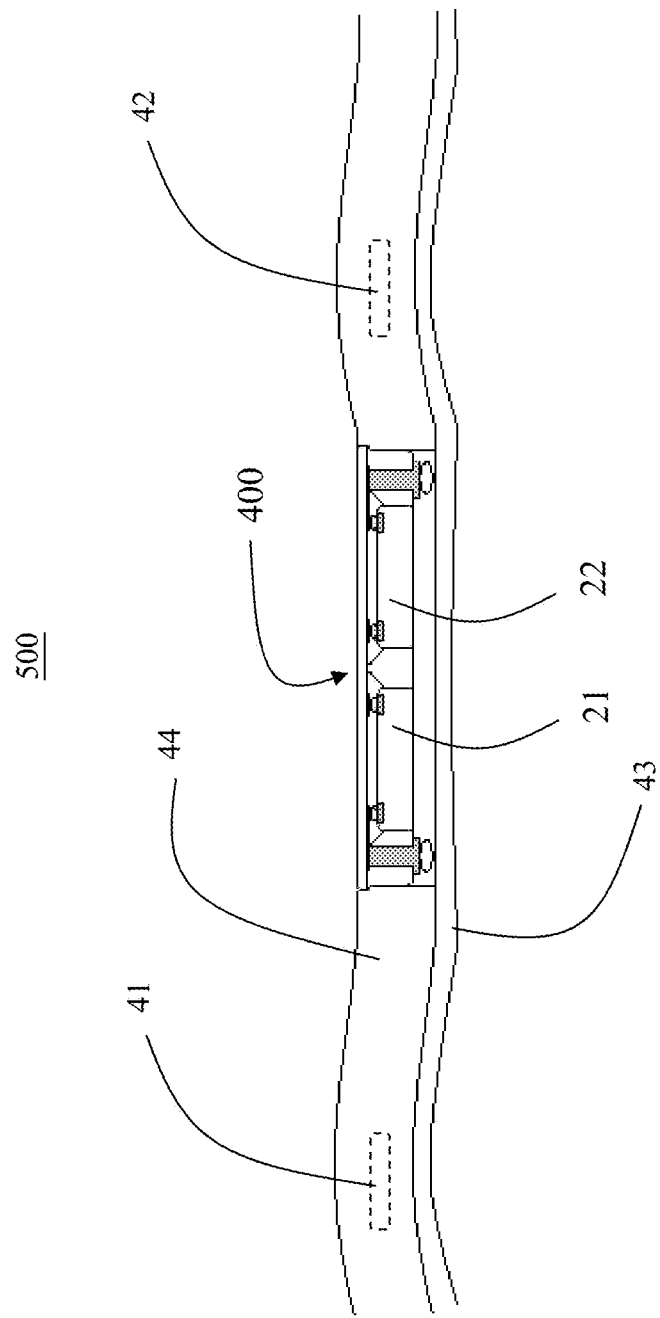
FIG. 5 shows a wristband embedding the reflective sensing module according to the present invention.

FIG. 5 shows a wristband embedding the reflective sensing module according to the present invention.

FIG. 5 shows a wristband 500 embedding the reflective sensing module 400 according to the present invention. A flexible circuit board 43 is prepared and electrically coupled to the reflective sensing module 400. A control chip 41 is configured and electrically coupled to the flexible circuit board 43, and a flexible molding compound 44 encloses the reflective sensing module 400 and the control chip 41. A transceiver (not shown) can be integrated in the control chip 41 for an information exchange. A battery 42 can also be prepared and embedded in the molding compound 44 to provide the power needed for the control chip 41.

Figure 6:
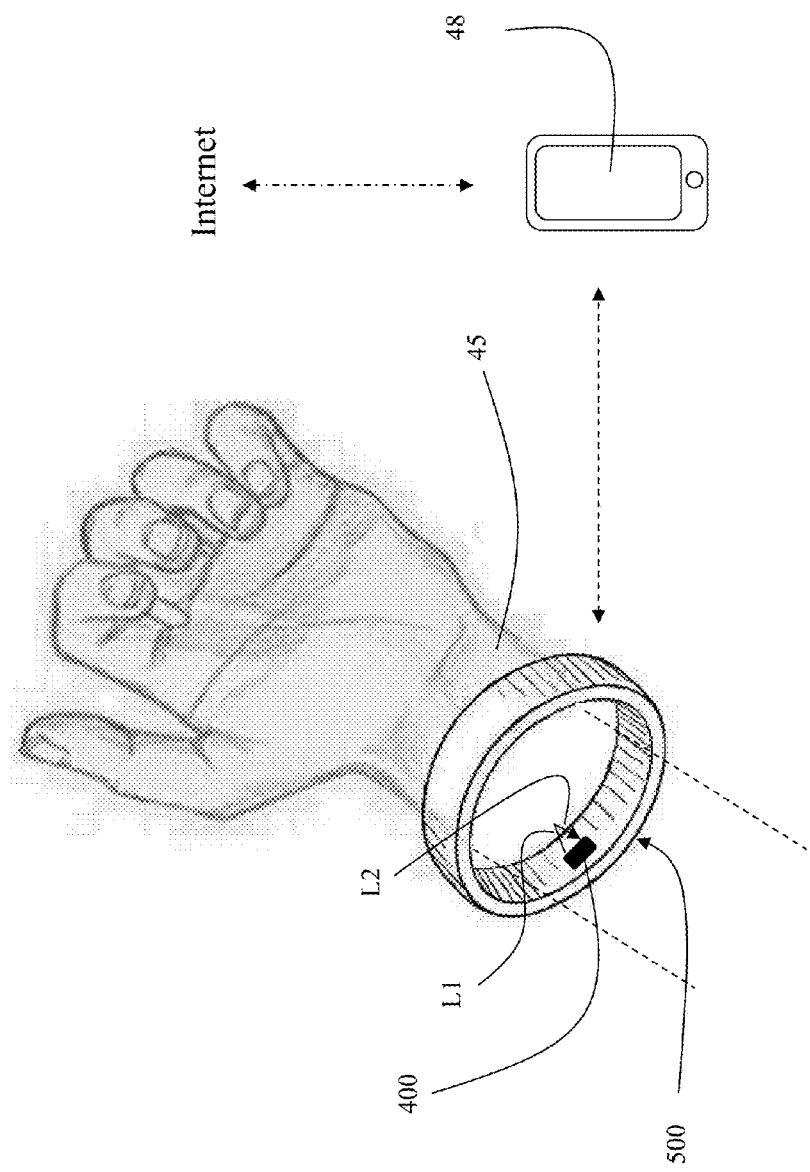
FIG. 6 shows a wristband wearing on a wrist according to the present invention.

FIG. 6 shows a wristband wearing on a wrist according to the present invention.

FIG. 6 shows a flexible wristband 500 worn on a wrist. The plurality of light beams L1 emitted from the light chip 21 detects health information such as pulse rate of blood vessels. The health information detected by the sensor chip 22 is transmitted to a mobile phone 48 through the transducer in the control chip 41. The mobile phone 48 is then connected to internet for transmitting the health information to a predetermined host computer, for example, located in a hospital where the information can be retrieved for a reference, or transmitted to a mobile phone of a doctor for the doctor's reference.

While several embodiments have been described by way of example, it will be apparent to those skilled in the art that various modifications may be configured without departs from the spirit of the present invention. Such modifications are all within the scope of the present invention, as defined by the appended claims.

What is claimed is:

1. A reflective sensing module, comprising:
 a top cover which is transparent;
 a first bottom circuitry on a bottom surface of the top cover;
 a light chip having first top electrodes on a top surface of the light chip, the first top electrodes being physically attached and electrically coupled to the first bottom circuitry; and
 a sensor chip having second top electrodes on a top surface of the sensor chip, the second top electrodes being physically attached and electrically coupled to the first bottom circuitry; wherein
 the light chip is configured to emit light beams upwards passing through the top cover to an object, and
 the sensor chip is configured to detect light beams reflected downwards from the object and passing through the top cover for a further processing.

2. The reflective sensing module as claimed in claim 1, further comprising:
 a molding compound enclosing the light chip and the sensor chip;
 a second bottom circuitry on a bottom surface of the molding compound; and
 a plurality of via metals passing through the molding compound, and electrically coupling the first bottom circuitry with the second bottom circuitry.

3. The reflective sensing module as claimed in claim 2, further comprising:
 a redistribution circuitry on bottom of the second bottom circuitry;
 a plurality of bottom pads on bottom of the redistribution circuitry; and
 a plurality of solder balls, each on one corresponding bottom pad among the plurality of bottom pads.

4. The reflective sensing module as claimed in claim 1, further comprising:
 a molding compound enclosing side surfaces while exposing a bottom surface of each of the light chip and the sensor chip;
 a plurality of bottom pads on a bottom surface of the molding compound; and
 a plurality of solder balls, each on one corresponding bottom pad among the plurality of bottom pads.

5. The reflective sensing module as claimed in claim 1, wherein the top cover comprises:
 a first Fresnel lens on top of the light chip; and
 a second Fresnel lens on top of the sensor chip.

6. A wristband, comprising:
 a reflective sensing module, comprising:
  a top cover;
  a bottom circuitry configured on a bottom surface of the top cover;
  a light chip electrically coupled to the bottom circuitry of the top cover;
  a sensor chip electrically coupled to the bottom circuitry of the top cover;
  a first Fresnel lens configured on top of the light chip; and
  a second Fresnel lens configure on top of the sensor chip, wherein
  the light chip is able to emit light beams upwards passing through the top cover to an object;
  the sensor chip is able to detect reflective light beams downwards passing through the top cover for a further processing;
 a flexible circuit board electrically coupled to the reflective sensing module;
 a control chip electrically coupled to the flexible circuit board; and
 a flexible molding compound enclosing the reflective sensing module and the control chip.

7. The wristband as claimed in claim 6, wherein the wristband has a shape of a closed loop.

8. The wristband as claimed in claim 7, wherein the closed loop of the wristband has a size adapted to be worn on a wrist of a user.

9. The wristband as claimed in claim 8, wherein the closed loop of the wristband has
an outer side adapted to face away from the wrist when the wristband is worn on the wrist, and
an inner side adapted to face toward the wrist when the wristband is worn on the wrist, wherein the top cover of the reflective sensing module is on the inner side.

10. The reflective sensing module as claimed in claim 1, further comprising:
a molding compound enclosing the light chip and the sensor chip, wherein the molding compound is in contact with side surfaces of the light chip and side surfaces of the sensor chip, and the molding compound has
a top surface in contact with the first bottom circuitry, and
a bottom surface; and
a plurality of via metals electrically coupled to the first bottom circuitry, and extending from the top surface of the molding compound through an entire thickness of the molding compound to the bottom surface of the molding compound.

11. The reflective sensing module as claimed in claim 10, further comprising:
a second bottom circuitry on the bottom surface of the molding compound, wherein
the plurality of via metals electrically couple the first bottom circuitry with the second bottom circuitry.

12. The reflective sensing module as claimed in claim 11, wherein
the bottom surface of the molding compound is below entireties of the light chip and the sensor chip, and
the molding compound is in contact with a bottom surface of the light chip and a bottom surface of the sensor chip.

13. The reflective sensing module as claimed in claim 12, further comprising:
a redistribution circuitry on bottom of the second bottom circuitry, wherein the redistribution circuitry has a plurality of bottom pads; and
a plurality of solder balls, each on one corresponding bottom pad among the plurality of bottom pads.

14. The reflective sensing module as claimed in claim 13, wherein
the plurality of solder balls is below an entirety of the molding compound.

15. The reflective sensing module as claimed in claim 14, wherein, in a cross section view of the reflective sensing module,
the plurality of solder balls, the light chip and the sensor chip are arranged in a middle portion of the reflective sensing module, and
the plurality of via metals is arranged in a peripheral portion of the reflective sensing module, wherein the peripheral portion surrounds the middle portion.

16. The reflective sensing module as claimed in claim 10, wherein
the molding compound exposes bottom surfaces of the light chip and the sensor chip,
the bottom surface of the molding compound is flush with the bottom surfaces of the light chip and the sensor chip,
the reflective sensing module further comprises a plurality of bottom pads on the bottom surface of the molding compound, and
the plurality of via metals electrically couple the first bottom circuitry with the plurality of bottom pads.

17. The reflective sensing module as claimed in claim 16, further comprising:
a plurality of solder balls, each on one corresponding bottom pad among the plurality of bottom pads,
wherein the plurality of solder balls is below an entirety of the molding compound.

18. The reflective sensing module as claimed in claim 17, wherein, in a cross section view of the reflective sensing module,
the light chip and the sensor chip are arranged in a middle portion of the reflective sensing module, and
the plurality of solder balls and the plurality of via metals are arranged in a peripheral portion of the reflective sensing module, wherein the peripheral portion surrounds the middle portion.

19. The reflective sensing module as claimed in claim 10, further comprising:
underfill material filled in
a first gap between the bottom surface of the top cover and the top surface of the light chip, and
a second gap between the bottom surface of the top cover and the top surface of the sensor chip, wherein
the molding compound is in contact with the underfill material.

20. A wristband, comprising:
the reflective sensing module as claimed in claim 1;
a flexible circuit board electrically coupled to the reflective sensing module;
a control chip electrically coupled to the flexible circuit board; and
a flexible molding compound enclosing the reflective sensing module and the control chip, wherein
the wristband has a shape of a closed loop of a size adapted to be worn on a wrist of a user, and the closed loop of the wristband has
an outer side adapted to face away from the wrist when the wristband is worn on the wrist, and
an inner side adapted to face toward the wrist when the wristband is worn on the wrist, wherein the top cover of the reflective sensing module is on the inner side.

* * * * *